United States Patent [19]

Livak et al.

[11] Patent Number: 5,126,239
[45] Date of Patent: Jun. 30, 1992

[54] PROCESS FOR DETECTING POLYMORPHISMS ON THE BASIS OF NUCLEOTIDE DIFFERENCES

[75] Inventors: Kenneth J. Livak; Jan A. Rafalski, both of Wilmington, Del.; Scott V. Tingey, Elkon, Md.; John G. Williams, Landenberg, Pa.

[73] Assignee: E. I. Du Pont de Nemours and Company, Wilmington, Del.

[21] Appl. No.: 494,258

[22] Filed: Mar. 14, 1990

[51] Int. Cl.$^5$ .................. C12Q 1/68; G01N 33/48; G01N 33/566; C12P 19/34
[52] U.S. Cl. .................. 435/6; 435/91; 436/94; 436/501; 935/77; 935/78
[58] Field of Search .................. 435/6, 91; 436/501, 436/94; 935/77, 78

[56] References Cited

U.S. PATENT DOCUMENTS 4,683,195 7/1987 Mullis et al. .................. 435/6
4,683,202 7/1987 Mullis .................. 435/91

FOREIGN PATENT DOCUMENTS 395398 10/1990 European Pat. Off. .................. 435/91

OTHER PUBLICATIONS

Syvänen et al., Nuc. Acids Res. 16(23): 11327–11338 (1988).
Engelke, et al., Proc. Natl. Acad. Sci. USA, 85: 544–548 (1988).
Wong, et al., Nature 330: 384–386 (1987).
Botstein, et al., Am. J. Hum. Genet., 32: 314–331 (1980).
White, et al., Sci. Am., 258: 40–48 (1988).
Jeffreys, Cell, 18: 1–18 (1979).
Proudfoot, et al., Science, 209: 1329–1336 (1980).
Skolnic and Wallace, Simultaneous Analysis of Multiple Polymorphic Loci Using Amplified Sequence Polymorphisms (ASPs), Genomics 2: 273–278.
Dear and Cook, Nucleic Acids Research, vol. 17, No. 17, 6795–6807 (1989).
M. G. Murray, et al., Nucleic Acids Research, vol. 8, No. 19 (1980) pp. 4321–4325.
Molecular Biology of Plants–A Laboratory Course Manual (1984) pp. 36–37.

*Primary Examiner*—Robert A. Wax
*Assistant Examiner*—Stephanie W. Zitomer

[57] ABSTRACT

A process is provided for detecting polymorphisms on the basis of nucleotide differences in random segments of the nucleic acid by performing a primer extension reaction on the nucleic acids and comparing the extension reaction products. The random nucleic acid segment can be amplified by first dissociating the extension product from the template and contacting the dissociated extension product with a primer under conditions such that an amplification extension product is synthesized using the dissociated extension product as a template. Differences in the extension product are useful as markers in constructing genetic maps and as markers to distinguish or identify individuals.

18 Claims, 11 Drawing Sheets

PROCESS FOR DETECTING POLYMORPHISMS ON THE BASIS OF NUCLEOTIDE DIFFERENCES

FIELD OF THE INVENTION

This invention relates to a process for distinguishing nucleic acids. More particularly, random nucleic acid segments are distinguished by comparing nucleotide differences in extension reaction products.

BACKGROUND OF THE INVENTION

The science of genetics is based on the identification and characterization of mutations, which are changes in DNA (DNA polymorphisms) due to nucleotide substitution, insertion, or deletion. Many techniques have been developed to compare homologous segments of DNA to determine if the segments are identical or if they differ at one or more nucleotides. Practical applications of these techniques include genetic disease diagnoses, forensic techniques, human genome mapping and agricultural applications.

The most definitive method for comparing DNA segments is to determine the complete nucleotide sequence of each segment. Examples of how sequencing has been used to study mutations in human genes are included in the publications of Engelke et al., *Proc. Natl. Acad. Sci. U.S.A.*, 85:544-548 (1988) and Wong et-al., *Nature* 330:384-386 (1987). At the present time, it is not practical to use extensive sequencing to compare more than just a few DNA segments, because the effort required to determine, interpret, and compare sequence information is extensive.

For genetic mapping purposes, the most commonly used screen for DNA polymorphisms arising from mutation consists of digesting DNA with restriction endonucleases and analyzing the resulting fragments, as described by Botstein et al., *Am. J. Hum. Genet.*, 32:314-331 (1980); White, et al., *Sci Am.*, 258:40-48 (1988). Mutations that affect the recognition sequence of the endonuclease will preclude enzymatic cleavage at that site, thereby altering the cleavage pattern of the DNA. DNAs are compared by looking for differences in restriction fragment lengths. A major drawback to this method (known as restriction fragment length polymorphism mapping or RFLP mapping) is its inability to detect mutations that do not affect cleavage with a restriction endonuclease. Thus, many mutations are missed with this method. One study by Jeffreys, *Cell*, 18:1-18 (1979), was able to detect only 0.7% of the mutational variants estimated to be present in a 40,000 base pair region of human DNA. Another difficulty is that the methods used to detect restriction fragment length polymorphisms are very labor intensive, in particular, the techniques involved with Southern blot analysis.

The primer extension process described in Proudfoot et al., *Science* 209:1329-1336 (1980), has been widely used to study the structure of RNA and also has been used to characterize DNA, see, e.g., Engelke et al., *Proc. Natl. Acad. Sci. U.S.A.*, 85:544-548 (1988). This process consists of hybridizing a labeled oligonucleotide primer to a template RNA or DNA and then using a DNA polymerase and deoxynucleoside triphosphates to extend the primer to the 5' end of the template. The labeled primer extension product is then fractionated on the basis of size, usually by electrophoresis through a denaturing polyacrylamide gel. When used to compare homologous DNA segments, this process can detect differences due to nucleotide insertion or deletion. Because size is the sole criterion used to characterize the primer extension product, this method cannot detect differences due to nucleotide substitution.

Mullis et al., U.S. Pat. No. 4,683,195, and Mullis, U.S. Pat. No. 4,683,202 disclose polymerase chain reactions which can be used to amplify any specific segment of a nucleic acid. These analytical methods have been used to detect polymorphisms through amplification of selected target DNA segments from test genomes. A drawback to such methods is the requirement that a sufficient number of bases at both ends of the specific segment be known in sufficient detail so that two oligonucleotide primers can be designed which will hybridize to different strands of the target segment. It is labor intensive to obtain the necessary sequence information from target genomes in order to design the necessary primers. M. H. Skolnic and R. B. Wallace, Simultaneous Analysis of Multiple Polymorphic Loci Using Amplified Sequence Polymorphisms (ASPs), *Genomics* 2:273-278.

Amplification using oligonucleotides of random sequence is described in a theoretical approach for mapping a genome of a higher eukaryote in "Happy Mapping: a Proposal for Linkage Mapping the Human Genome," P. H. Dear and P. R. Cook, *Nucleic Acids Research*, Vol. 17, No. 17, 6795-6807 (1989). The authors propose to identify the relationship between 5,000 different DNA segments amplified from human genomic DNA by performing a polymerase chain reaction (PCR) with various pairwise combinations of arbitrary-sequence primers. The template DNA is isolated separately from single haploid cells of an individual organism. Their method suggests generating a map describing the physical location of DNA regions giving rise to the amplified products in an individual organism. This would be accomplished by identifying PCR products which co-amplify from the same piece of DNA, thus establishing their physical proximity. In Dear and Cook's method, polymorphisms would be excluded from the analysis. Their idea requires the identification of the same DNA segment in many different haploid cells, and polymorphisms defeat this requirement. Although efficient at describing the physical relationship between any two PCR products, happy mapping cannot describe the location of any genetic traits of interest. This can only be accomplished by correlating the segregation of a genetic trait with many different polymorphisms through a sexual cross between two individuals. The authors teach that primer pairs longer than 9-10 nucleotides are necessary as primer pairs of 9-10 nucleotides would prime inefficiently.

The present invention provides a process for the detection of genetic polymorphisms in random nonspecific nucleic acid segments. The process utilizes a reaction primed by an oligonucleotide(s) conveniently prepared with no knowledge of the base sequence of segments amplified.

SUMMARY OF THE INVENTION

The present invention provides a process for distinguishing nucleic acids on the basis of nucleotide differences in random segments of the nucleic acid comprising:

(a) separately performing an extension reaction on each of at least two nucleic acids, said reaction comprising:

(i) contacting the nucleic acids with at least one oligonucleotide primer of greater than 7 nucleotides under conditions such that for at least one nucleic acid an extension product of at least one primer is synthesized; and (b) comparing the results of the separately performed extension reactions for differences.

In another aspect of this invention, after step (i) and before step (b), there are provided the additional steps of (ii) dissociating the extension product from its complement; and (iii) amplifying the random nucleic acid segment by contacting the dissociated extension product with a primer of step (i) under conditions such that an amplification extension product is synthesized using the dissociated extension product as a template.

In another aspect of this invention, a difference in the extension product is used as a marker to construct a genetic map, and to distinguish or identify individuals.

BRIEF DESCRIPTION OF THE DRAWINGS

FIGS. 3A and 3 B illustrate a photograph of a gel comparing amplification products from Bonus (odd-numbered lanes) and PI 81762 (even-numbered lanes). Primer AP8 and 10 other primers differing in a single nucleotide from AP8 were employed.

DETAILED DESCRIPTION OF THE INVENTION

The term "oligonucleotide" as used herein refers to a molecule comprised of two or more deoxyribonucleotides or ribonucleotides.

The term "primer" as used herein refers to an oligonucleotide of any arbitrary sequence whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. It is preferable that primers are sequences that do not form a secondary structure by base pairing with other copies of the primer or sequences that form a "hair pin" configuration. The sequence conveniently can be generated by computer or selected at random from a gene bank. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide.

The term "random nucleic acid segment" as used herein refers to any template, the segment of nucleic acid to be addressed by the primer, of which no sequence information need be known prior to extension. Applicants have found that it is not required, with the process of this invention, that a sufficient number of bases at both ends of a template be known in sufficient detail so that primers can be designed which will hybridize to different strands of the template.

In the process of the present invention, at least one primer of greater than 7 nucleotides is provided. Primers with less than 7 nucleotides prime inefficiently. Primers can be synthesized by standard techniques known to those skilled in the art. In the preferred form of the invention, at least one primer of 9 to 10 nucleotides in length is employed. Conveniently, one primer is employed. At least one primer employed may be biotinylated. That is, the primer may be covalently linked to a biotin or an analog of biotin. The linking group employed should be chosen to permit extension under the conditions detailed herein.

The process of the present invention for distinguishing nucleic acids compares differences in products of an extension reaction(s) separately performed on at least two random segments of nucleic acids.

In the first step of the present process, an extension reaction is (a) separately performed on each of at least two nucleic acids by (i) contacting the nucleic acids with at least one oligonucleotide primer of greater than 7 nucleotides under conditions such that for at least one nucleic acid an extension product of at least one primer is synthesized which is complementary to the random nucleic acid segment. A preferred embodiment of this extension reaction exploits the ability of most DNA polymerases to perform primer extension reactions. Execution of a primer extension reaction requires a nucleic acid substrate consisting of a primer hybridized to a template strand such that the 3' end of the primer is recessed relative to the 5' end of the template strand. As primer extension methods are most commonly practiced, the primer is DNA, the template strand is either DNA or RNA, and a DNA polymerase is used to extend the primer. The basic elements required for execution of primer extension reactions are reviewed in Mullis et al., U.S. Pat. No. 4,683,195, and Mullis, U.S. Pat. No. 4,683,202.

The nucleic acids to be analyzed by this process may be DNA or RNA, and the DNA or RNA may be double stranded or single stranded. Any source of nucleic acid, in purified or nonpurified form, can be utilized as the starting nucleic acid. For example the nucleic acid may be from a natural DNA or RNA from any source, including virus, bacteria, and higher organisms such as plants, animals and microbes or from cloned DNA or RNA. Additionally, the nucleic acid may constitute the entire nucleic acid or may be a fraction of a complex mixture of nucleic acids. Preferably the nucleic acid is deoxyribonucleic acid. Surprisingly, Applicants have found the process of the present invention useful in distinguishing nucleic acids from different individual organisms containing small genomic DNA such as yeast DNA ($2 \times 10^7$ base pairs per genome) as well as different individual organisms containing large genomic DNA such as human DNA ($3.0 \times 10^9$ base pairs per genome).

The choice of nucleic acid polymerase used in the extension reaction, depends on the nature of the template. For DNA template strands, suitable commercially available DNA polymerase includes DNA polymerase obtained from the thermophilic bacterium *Thermus aquaticus* (Taq polymerase) or other thermostable polymerases. Structural variants and modified forms of this and other DNA polymerases would also be expected to be useful in the process of the present invention. For RNA templates, reverse transcriptase is an example of a DNA polymerase that would also be expected to be useful. In the presence of the nucleoside triphosphate substrates, natural or analogues, the polymerase extends the length of the primer in the 3' direction. The sequence of the extension product will generally be complementary to the corresponding sequence of the template strand.

The nucleoside triphosphate substrates are employed as described in *PCR Protocols, A Guide to Methods and Applications*, M. A. Innis, D. H. Gelfand, J.-J. Sninsky and T. J. White, eds. pp. 3-12, Academic Press (1989), which is incorporated by reference, and U.S. Pat. Nos. 4,683,195 and 4,683,202. The substrates can be modified for a variety of experimental purposes in ways known to those skilled in the art. As an example, at least one of the natural nucleoside triphosphate substrates may be replaced by a mobility-shifting analogue as taught in U.S. Pat. No. 4,879,214 which patent is incorporated by reference.

In another aspect of this invention, after step (i) is performed, the additional steps of (ii) dissociating the extension product from its complement; and (iii) amplifying the random nucleic acid segment by contacting the dissociated extension product with a primer of step (i) under conditions such that an amplification extension product is synthesized using the dissociated extension product as a template are performed.

An amplification reaction is generally described in Mullis et al., U.S. Pat. No. 4,683,195 and Mullis, U.S. Pat. No. 4,683,202, which patents are incorporated by reference. Specific conditions for amplifying a nucleic acid template are described in M. A. Innis and D. H. Gelfand, *PCR Protocols, A Guide to Methods and Applications*, M. A. Innis, D. H. Gelfand, J.-J. Sninsky and T. J. White, eds. pp. 3-12, Academic Press (1989), which is incorporated by reference.

Specifically, Mullis is directed to a process for amplifying any desired specific nucleic acid sequence contained in a nucleic acid or mixture thereof. The process of Mullis comprises treating separate complementary strands of the nucleic acid with a molar excess of two oligonucleotide primers, and extending the primers to form complementary primer extension products which act as templates for synthesizing the desired nucleic acid sequence. The primers of Mullis are designed to be sufficiently complementary to different strands of each specific sequence to be amplified. The steps of the reaction may be carried out stepwise or simultaneously and can be repeated as often as desired.

In the extension reactions of the present invention, a nucleic acid is contacted with at least one oligonucleotide primer as described herein. The extension product is dissociated from the complementary random nucleic acid on which it was synthesized to produce a single-stranded molecule; and the random nucleic acid segment is amplified by contacting the single-stranded extension product with a primer from above under conditions as for example disclosed in PCR Protocols and U.S. Pat. No. 4,683,202 such that an amplification extension product is synthesized using the single strand produced (i.e., the dissociated extension product) as a template.

The steps described herein may be conducted sequentially or simultaneously as taught by U.S. Pat. Nos. 4,683,195 and 4,683,202. In addition, the steps may be repeated until the desired level of sequence amplification is obtained as taught by U.S. Pat. Nos. 4,683,195 and 4,683,202.

Following extension, the results of step (b) are compared for differences. Generally the results are products or an absence of product. Specifically, the products are compared to determine if the segments are identical or for differences in one or more nucleotides, by nucleotide substitution, insertion or deletion. Differences in the products can take the form of, for example, difference in size of each product, difference in the sequence of each product, difference in the quantity of each product produced, and differences in the number of products.

Comparison of the product can be accomplished by a variety of techniques known to those skilled in the art. Examples include nucleotide sequence determination of the amplified segment and RFLP analysis. Conveniently, comparison can be through a size fractionation medium. If the resolution of the size fractionation process is sufficient, differences of a single nucleotide can be detected. The preferred process for size fractionation is electrophoresis through a polyacrylamide or agarose gel matrix.

Simple inspection of the electrophoresis gel of the product can reveal polymorphisms that affect the size and quantity of the amplified segment and polymorphisms that determine whether a segment is amplified. Polymorphisms revealed by the present invention can be quantified by known densitometric procedures performed on the amplified product in the gel. Quantification is important in certain applications where it is necessary to distinguish homozygous from heterozygous polymorphisms. Applicants have found that a homozygote with two copies of the polymorphism generates twice as much of the product than does a heterozygote.

The process of the present invention has practical applications. Examples of such applications include genetic mapping and distinguishing and identifying individuals.

Applicants have found that the polymorphisms or differences identified through the process of this invention can have utility in genetic mapping. Commonly, a genetic map is constructed by through RLFP analysis. A genetic map of an organism could be constructed, e.g. by substituting polymorphisms, identified using different primers on the same organism, detected by the present invention for the RFLPs used as genetic markers as described in the art, e.g., Botstein, D., "Construction of a Genetic Linkage Map in Man Using Restriction Fragment Length Polymorphisms", *Am. J. Hum. Genet.* 32:314-331, (1980) which reference is incorporated herein. Genetic mapping using the polymorphisms of the present invention as markers has important plant breeding applications as Applicants have determined that polymorphisms detected by the present invention are heritable genetic markers. These markers, just as RFLP markers in Tanksley, S. D., "RFLP Mapping in Plant Breeding: New Tools for an Old Science", Bio/-Technology Vol. 7 March, 1989, pp.257-264, can be used as probes for the presence or absence of certain chromosome segments as Applicants have found that the polymorphisms detected by the process of the present invention can co-segregate with standard RFLP markers.

Further, the process of the present invention can be used to construct a nucleic acid 'fingerprint'. Such fingerprints are specific to individuals and can be applied to problems of identification or distinguishing of individuals. Such a 'fingerprint' would be constructed using multiple polymorphisms generated by different primers and detected by the present invention, just as the polymorphisms are used to create a fingerprint in Jeffreys, A. J., "Individual-Specific 'Fingerprints' of Human DNA", Nature, Vol. 316 Jul. 4, 1985 which reference is incorporated herein. That is, genomes are compared for the presence of absence of polymorphisms.

EXAMPLES

Example 1 demonstrates synthesis and purification of oligonucleotide primers. Example 2 shows that a variety of 10 nucleotide primers are able to amplify random nucleic acid segments, and that polymorphisms can be detected between genomic DNA samples from two soybean cultivars. Example 3 illustrates that polymorphisms revealed by this invention are inherited in normal fashion by the progeny of a cross between two soybean lines. This example establishes the utility of the polymorphisms as genetic markers. Example 4 shows that the pattern of amplified bands is specific to a given primer sequence. Most changes involving a single nucleotide in the primer sequence cause a complete alteration in the pattern of amplified DNA segments. This suggests that most single-nucleotide polymorphisms at corresponding priming sites in individual genomes will be seen by the process of the present invention as a difference in the pattern of amplified DNA segments. Example 5 illustrates that 10 nucleotide primers amplify generally equivalent numbers of DNA segments from both small and large genomes. Example 6 demonstrates the utility of primers of from 6 to 10 nucleotides in length. Example 8 shows the process of the present invention detects a polymorphism that can be used to distinguish human DNA samples. Example 9 shows quantitation of the amplification products.

EXAMPLE 1

Synthesis and purification of oligonucleotide primers

Eight oligonucleotide primers (Table I) were synthesized by standard solid-phase methods with phosphoramidite chemistry in a Du Pont Model Coder 300 automated DNA synthesizer (E. I. du Pont de Nemours and Company, Wilmington, Del.). The eight primers were of arbitrary nucleotide sequence. Each primer was selected to contain the same proportion of the bases A and T as the bases G and C for generally equal stability when attached to the template.

After deprotection in ammonium hydroxide according to standard practice, the samples were dried under vacuum, dissolved in 0.2 ml of TEN (10 mM Tris-Cl, pH 7.5, 1 mM NaEDTA, 10 mM NaCl) and purified by gel filtration chromatography on Sephadex G25 in NAP-5 cartridges (Pharmacia, Piscataway, N.J.) equilibrated in TEN. Gel filtration was accomplished by applying 0.2 ml of sample; followed by 0.6 ml of TEN, followed by 0.5 ml of TEN applied to the top of the column and collecting 0.5 ml of eluant. The concentration of purified oligonucleotide was calculated by absorbance at 260 nm on a spectrophotometer. An absorbance value of 1 corresponding to 33 µg/ml was assumed.

TABLE I

| Primer sequence | Primer name | Concentration of stock solution µg |
|---|---|---|
| 5'-AGCACTGTCA | 10b | 10 |
| 5'-TCGTAGCCAA | AP3 | 10 |
| 5'-TCACGATGCA | AP4 | 10 |
| 5'-CTGATGCTAC | AP5 | 10 |
| 5'-GCAAGTAGCT | AP6 | 10 |
| 5'-CTGATACGGA | AP7 | 10 |
| 5'-TGGTCACTGA | AP8 | 10 |
| 5'-ACGGTACACT | AP9 | 10 |

EXAMPLE 2

Primers (Table I) detect polymorphisms in soybean DNA templates

Genomic DNA was isolated from the soybean cultivars PI 81762 and Bonus by centrifugation in CSCl/ethidium bromide as described in Murray, M.G. "Rapid Isolation of High Molecular Weight Plant DNA", Nucleic Acids Res. Vol. 8 (1980) pp. 4321-4326 which reference is incorporated herein. The source of the soybean cultivars was Professor Theodore Hymowitz, University of Illinois.

Eight different oligonucleotides, each 10 nucleotides in length (Table I) were tested separately as primers in the amplification reaction detailed below for their ability to amplify DNA segments from the two varieties of soybean DNA.

The process of the present invention was performed in a reaction volume of 50 µl containing genomic DNA cocktails of 10 mM Tris-Cl, pH 8.3, 50 mM KCl, 2.5 mM MgCl$_2$, 0.001% gelatin (Sigma, St. Louis, Mo. cat. (1990) no. G-2500), 0.1 µg of soybean DNA, 20 pmole of oligonucleotide, 200 µM each of the deoxynucleotide triphosphates, dATP, dCTP, dGTP, dTTP, and 1.25 units of Amplitaq DNA polymerase (Perkin-Elmer Cetus cat. no. N801-0060, Norwalk, Conn.). The genomic DNA cocktail was prepared by mixing ingredients 1-5 (Table II) and heating this mixture at 99° C. for 4 minutes in the heating block of a DNA thermal cycler. This mixture was then cooled to room temperature before the addition of ingredients 6 and 7 (Table II).

Amplification was conducted in 0.6 ml microcentrifuge tubes (cat. no. 1048-00-0 from Robbins Scientific Corp., 1280 Space Park Way, Mtn. View, Calif. 94943 (1990)) and the reaction was initiated by adding 48 µl of a genomic DNA cocktail (Table II) to 2 µl of each primer from Table I and overlayed with 40 µl of mineral oil (Sigma cat. no. M3516).

TABLE II

| | | Volume | |
|---|---|---|---|
| # | Genomic DNA cocktails | PI81762 µl | Bonus µl |
| 1 | Deionized water | 309.0 | 308.0 |
| 2 | 10x Buffer* | 45.0 | 45.0 |
| 3 | MgCl$_2$, 200 mM | 2.2 | 2.2 |
| 4 | PI 81762 DNA, 672 µg/ml | 1.3 | — |
| 5 | Bonus DNA, 448 µg/ml | — | 2.0 |
| 6 | Mixture of dATP, dCTP, dGTP, TTP, 1.25 mM each | 72.0 | 72.0 |
| 7 | Amplitaq polymerase, | 2.2 | 2.2 |

TABLE II-continued

| # | Genomic DNA cocktails | Volume | |
|---|---|---|---|
| | | PI81762 µl | Bonus µl |
| | 5 units/µl | | |

*10x Buffer consists of 100 mM TrisCl (pH 8.3), 500 mM KCl, 15 mM MgCl₂ and 0.01% Gelatin as directed in Perkin-Elmer Cetus cat. no. N 801-0060 Amplitaq DNA polymerase.

Temperature cycling in the amplification reaction was performed in a DNA Thermal Cycler (Perkin-Elmer Cetus, Norwalk, Conn.) for cycles with parameters set at: hold 94° C. for 1 min, hold 35° C. for sec, ramp to 72° C. in 1:51 min, hold 72° C. for 2 min.

Upon completion of the 16 separate amplification reactions performed above, 5 µl aliquots of each sample were analyzed by electrophoresis on a 1.4% agarose gel at 8.5 volt/cm for 60 minutes. Electrophoresis was conducted according to standard practice as described in J. Sambrook, E. F. Fritsch and T. Maniatis, *Molecular Cloning A Laboratory Manual*, Cold Spring-Harbor Laboratory Press, pp. 6.3–6.19 (1989), which is incorporated by reference. The gel was stained with ethidium bromide and was photographed.

Figure 1:
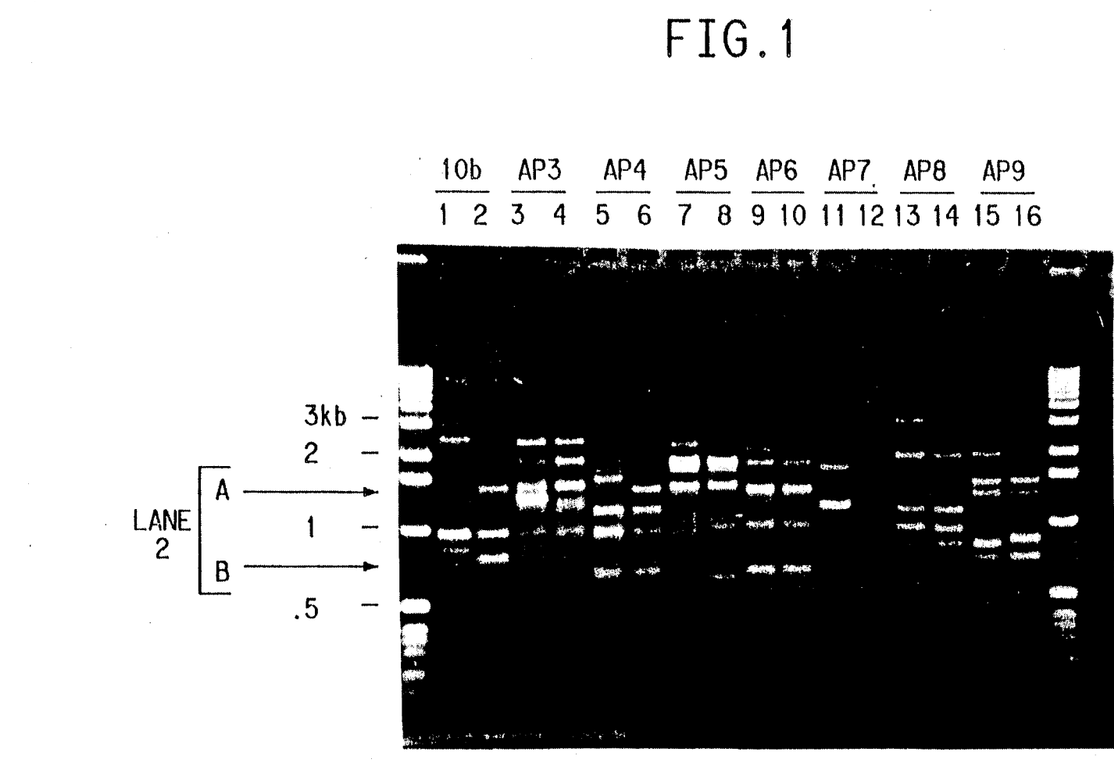
FIG. 1 illustrates a photograph of a gel comparing amplification products from DNA isolated from the soybeans *Glvine max* (Bonus) (odd-numbered lanes) and *Glycine soja* (PI 81762) (even-numbered lanes) where oligonucleotide primers of a variety of sequences were employed.
Figure 2A:
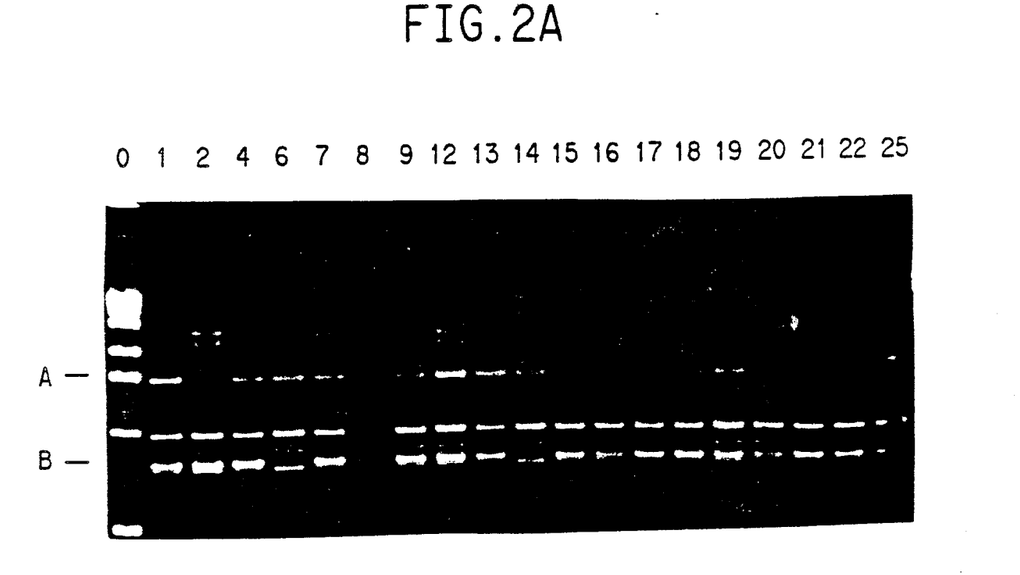
FIGS. 2A-2D illustrate a photograph of a gel comparing amplification products, utilizing primer 10b, of 19 F2 progeny of a cross between Bonus and PI 81762.
Figure 2B:
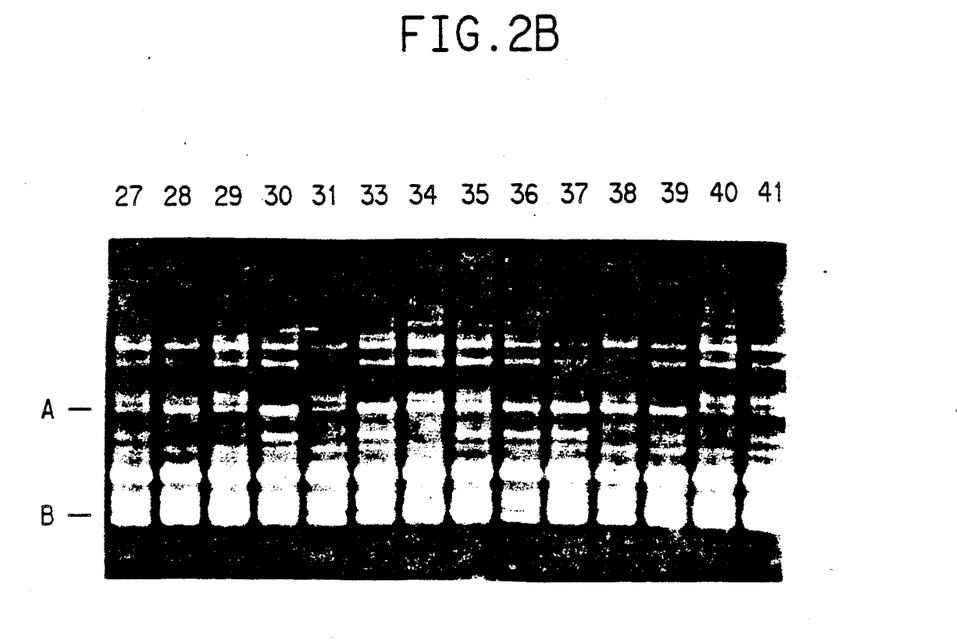
Figure 2C:
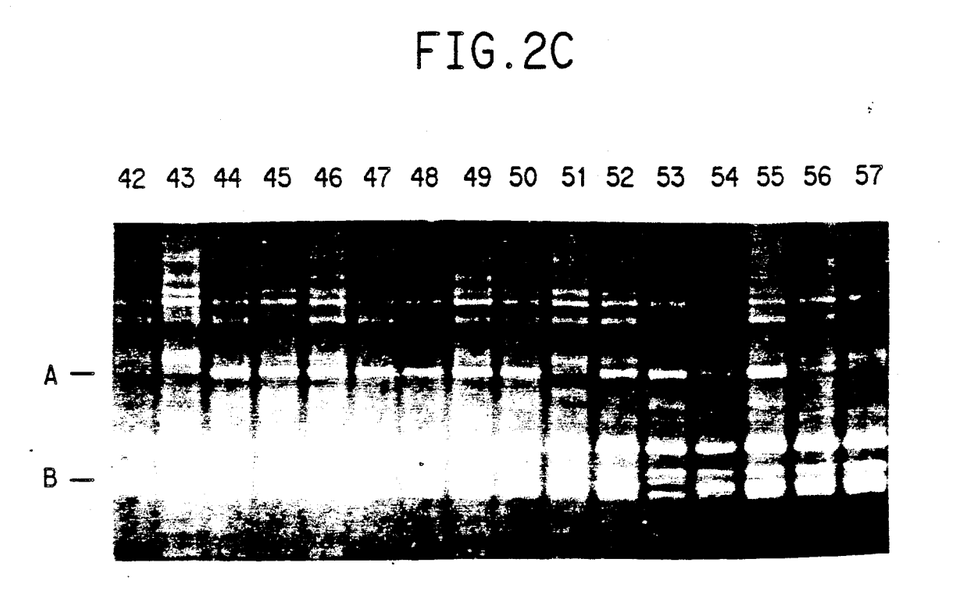
Figure 2D:
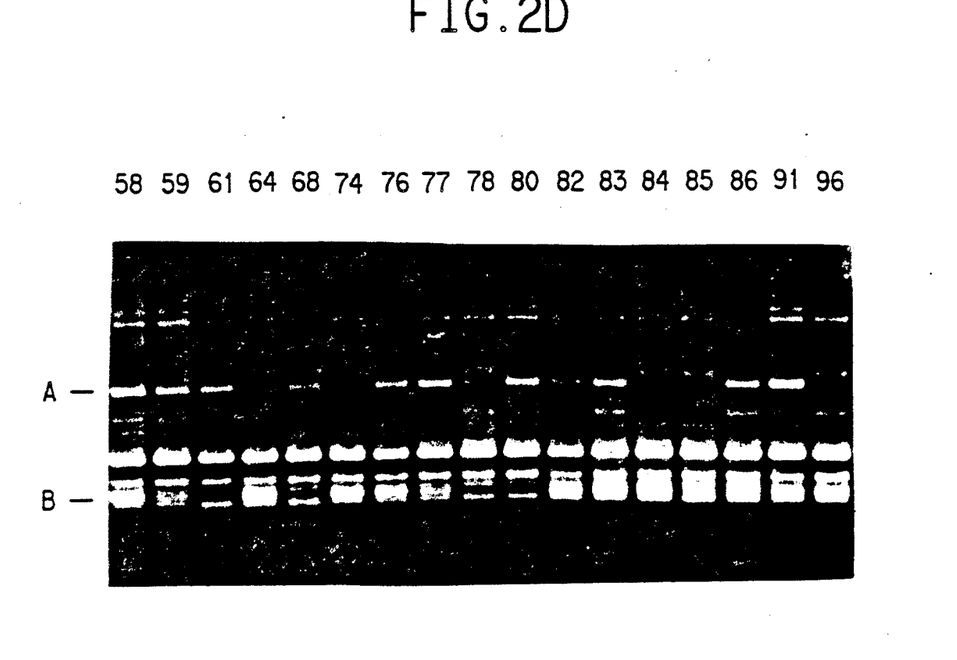

Polymorphisms, i.e., difference in the reaction product in the DNA patterns were evident for all primers except AP6 by comparing DNA bands amplified by a given primer from both Bonus and PI 81762 (FIG. 1). FIG. 1 is a photograph of the stained electrophoresis gel. Lane 0 is a molecular weight standard. Odd numbered lanes are the Bonus DNA amplification products from the eight primers (Table I) and even numbered Lanes are the PI 81762 DNA amplification products from the primers. It can be seen from the figure that random nucleic acid segments can be distinguished on the bases of nucleotide differences. As an example, two bands denoted "A" and "B" amplified by primer 10b were seen in DNA from PI 81762 (lane 2) but not from Bonus (lane 1).

EXAMPLE 3

Amplified polymorphisms are useful for genetic mapping

To determine whether such polymorphisms as seen in Example 2 have utility in genetic mapping, the band A polymorphism detected with primer 10b (FIG. 2) was mapped to the soybean genome. This was accomplished by scoring each of 66 segregating F₂ individuals (T. Hymowitz, U. of Ill.), for their parental pattern of inheritance of the band A polymorphism and correlating this with segregation data from the same 66 individuals for 430 RFLP markers previously mapped to the soybean genome (J. A. Rafalski and S. V. Tingey, Abstract, *Genome Mapping and Sequencing*, Apr. 26–30, 1989). Samples of the F₂ genomic DNA were subjected to the process of the present invention with primer 10b under the conditions described in Example 2 and analyzed by electrophoresis in a 1.4% agarose gel. Lane 0 is a molecular weight standard, and the remaining lanes are the reaction products of the F₂ individuals. Table 3 presents the parental pattern of inheritance for the primer 10b band A polymorphism. Since band A is amplified from PI81762 and not Bonus (FIG. 2), the presence of band A in a particular sample indicates that it received at least one copy of that DNA segment from PI81762. At first inspection it is difficult to distinguish between homozygotes that have received two copies of band A from PI81762 and heterozygotes that have received only one copy of band A from PI81762. Therefore this polymorphism is scored as a dominant marker (see legend to Table 3). Individuals that do not contain band A have inherited this segment of the genome from Bonus.

In order to determine the position of the band A locus in the soybean genome it was necessary to correlate the inheritance of this locus with that of several RFLP markers previously mapped to the soybean genome (J. A. Rafalski and S. V. Tingey, Abstract, *Genome Mapping and Sequencing*, Apr. 26–30, 1989). This genetic map (data not shown) was constructed by standard RFLP methodology from analysis of the segregation patterns of many RFLP markers in the same F₂ population as used in this example (for standard RFLP mapping technology, see T. Helentjaris, M. Slocum, S. Wright, A. Schaefer and J. Nienhuis, 1986, *Theor. Appl. Genet.*, 72:761–769 which reference is incorporated herein). The basis for genetic mapping analysis is that markers located near to each other in the genome are inherited together in the F₂ progeny, while markers located farther apart are co-inherited less frequently. Segregation analysis and marker map positions were calculated using the MapMaker program, incorporated herein (E. S. Lander, P. Green, J. Abrahamson, A. Barlow, J. F. Daly, S. E. Lincoln and L. Newburg, 1987, *Genomics* 1:174–181). The results indicate that the primer 10b band A polymorphism maps to linkage group 17 in between RFLP markers 249 and 7315 at a distance from each marker of 9.4 and 9.2 centimorgans, respectively. The probability that the band A polymorphism segregated purely by chance in the observed data was only 1 chance in $10^{-11.8}$ indicating the strength of this map position. This example demonstrates that polymorphisms as revealed by the present invention have utility as genetic markers.

TABLE III

| Marker Name | F₂ Individuals | | | | | | | | | | | | | | | | | | | | | | | | | | |
|---|---|---|---|---|---|---|---|---|---|---|---|---|---|---|---|---|---|---|---|---|---|---|---|---|---|---|---|
| | 1 | 2 | 4 | 5 | 6 | 7 | 8 | 9 | 12 | 13 | 14 | 15 | 16 | 17 | 18 | 19 | 20 | 21 | 22 | 23 | 25 | 26 | 27 | 28 | 29 | 30 | 31 |
| RFLP Marker 249 | B | A | H | H | H | H | A | H | B | H | H | H | A | H | H | H | A | H | A | H | m | H | A | H | A | B | A |
| RFLP Marker 7315 | B | A | H | m | H | A | H | H | B | B | H | A | H | H | H | H | A | H | H | m | H | m | m | H | A | B | A |
| Primer 10b Band A | b | A | b | m | b | b | m | b | b | b | b | A | A | A | b | b | A | b | A | m | b | m | A | b | A | b | A |

| Marker Name | F₂ Individuals | | | | | | | | | | | | | | | | | | | | | | | | | | |
|---|---|---|---|---|---|---|---|---|---|---|---|---|---|---|---|---|---|---|---|---|---|---|---|---|---|---|---|
| | 33 | 34 | 35 | 36 | 37 | 38 | 39 | 40 | 41 | 42 | 43 | 44 | 45 | 46 | 47 | 48 | 49 | 50 | 51 | 52 | 5 | 54 | 55 | 56 | 57 | 58 | 59 |
| RFLP Marker 249 | B | A | H | H | B | a | H | A | A | m | A | B | B | H | B | H | A | B | A | H | B | H | B | A | A | B | m |
| RFLP Marker 7315 | B | H | H | H | B | H | H | A | A | A | A | H | H | H | B | H | H | B | H | H | B | H | H | A | A | B | H |
| Primer 10b Band A | b | b | b | b | b | b | b | A | A | A | A | b | b | b | b | b | b | b | A | b | b | b | b | A | A | b | b |

TABLE III-continued

| Marker Name | F2 Individuals | | | | | | | | | | | | | | | | | | | | | | | | | |
|---|---|---|---|---|---|---|---|---|---|---|---|---|---|---|---|---|---|---|---|---|---|---|---|---|---|---|
| | 61 | 62 | 63 | 64 | 65 | 68 | 70 | 71 | 72 | 73 | 74 | 75 | 76 | 77 | 78 | 80 | 82 | 83 | 84 | 85 | 86 | 88 | 90 | 91 | 96 |
| RFLP Marker 249 | m | m | m | m | m | H | A | H | B | A | A | H | B | B | H | H | A | B | A | A | B | m | m | m | m |
| RFLP Marker 7315 | H | A | H | A | m | H | m | A | m | m | A | m | B | B | H | H | H | H | A | A | A | m | m | B | A |
| Primer 10b Band A | b | m | m | A | m | b | m | m | m | m | A | m | b | b | A | b | b | b | A | A | b | m | m | ⊢ | A |

Legend for Table III

DNA isolated from 88 $F_2$ individuals segregating from a cross between Bonus and PI81762. The genotype of each individual at each of the above marker loci was determined by either RFLP analysis or by the process of this invention (see text). Individual scores indicate the parental genotype of the marker locus. A score of "A" or "B" designates that the locus was inherited from Bonus or PI81762, respectively. A score of "H" designates that the locus was inherited both from Bonus and PI81762. A score of "a" designates that the locus was either inherited only from Bonus or that it was inherited from both Bonus and PI81762. A score of "b" designates that the locus was either inherited from PI81762 or that it was inherited from both Bonus and PI81762. A score of "m" designates missing data.

EXAMPLE 4

The pattern of amplification products of DNA segments is sensitive to single-nucleotide changes in the primer sequence A series of primers were synthesized based on the oligonucleotide primer AP8 of Example 2 (Table I). Each variant differed from the canonical sequence at a single nucleotide, progressing stepwise through the primer sequence. Nucleotide composition in each variant was maintained at 50% A+T as in Example 2. In Table IV, the nucleotide site that differs from the canonical sequence is shown in lower-case type.

TABLE IV

| Primer sequence | Primer name | Concentration of stock solution |
|---|---|---|
| 5'-TGGTCACTGA | AP8 (canonical) | 10 μM |
| 5'-aGGTCACTGA | AP8-a | 10 μM |
| 5'-TcGTCACTGA | AP8-b | 10 μM |
| 5'-TGcTCACTGA | AP8-c | 10 μM |
| 5'-TGGaCACTGA | AP8-d | 10 μM |
| 5'-TGGTgACTGA | AP8-e | 10 μM |
| 5'-TGGTCtCTGA | AP8-f | 10 μM |
| 5'-TGGTCAgTGA | AP8-g | 10 μM |
| 5'-TGGTCACaGA | AP8-h | 10 μM |
| 5'-TGGTCACTcA | AP8-i | 10 μM |
| 5'-TGGTCACTRGt | AP8-j | 10 μM |

Cocktails containing genomic DNA from Bonus and PI 81762 were prepared as described in Example 2 (Table II). However, instead of using microcentrifuge tubes as the reaction vessels for amplification, the samples were placed in the wells of a polyvinyl chloride (PVC) 96-well microtiter plate (Falcon, 1989, 3911, Becton Dickinson Labware, Oxnard, Calif.) and were overlaid with 40 μl of mineral oil (Sigma, St. Louis, Mo, cat. no. M3516 1990). Unused wells were filled with 50 μl of water plus 40 μl of oil. The 96-well plate was placed without a lid in an air-driven cycling oven (BSC 1000 with temperature probe BSC-2005, Bios Corp., 291 Whitney Ave., New Haven, Conn. 06511) atop a metal test tube rack with a 1-inch square grid. The rack was made 2" high by clipping the top tier from a three-tiered rack (4.75" wide×11.5" long×4" high). The freed tier was laid on top of the 96-well plate. The oven was in a room at an ambient temperature of 22° C. and was programmed for 35 cycles with the parameters: hold 93° C. for 1 min, hold 35° C. for 1 min, ramp to 72° C. in 2 min, hold 72° C. for 2 min. The soak tolerance was set at 2° C.

After the amplification reaction of the present invention was complete, 12 μl of each sample was analyzed by electrophoresis on a 1.4% agarose gel as described in Example 2.

Figure 3A:
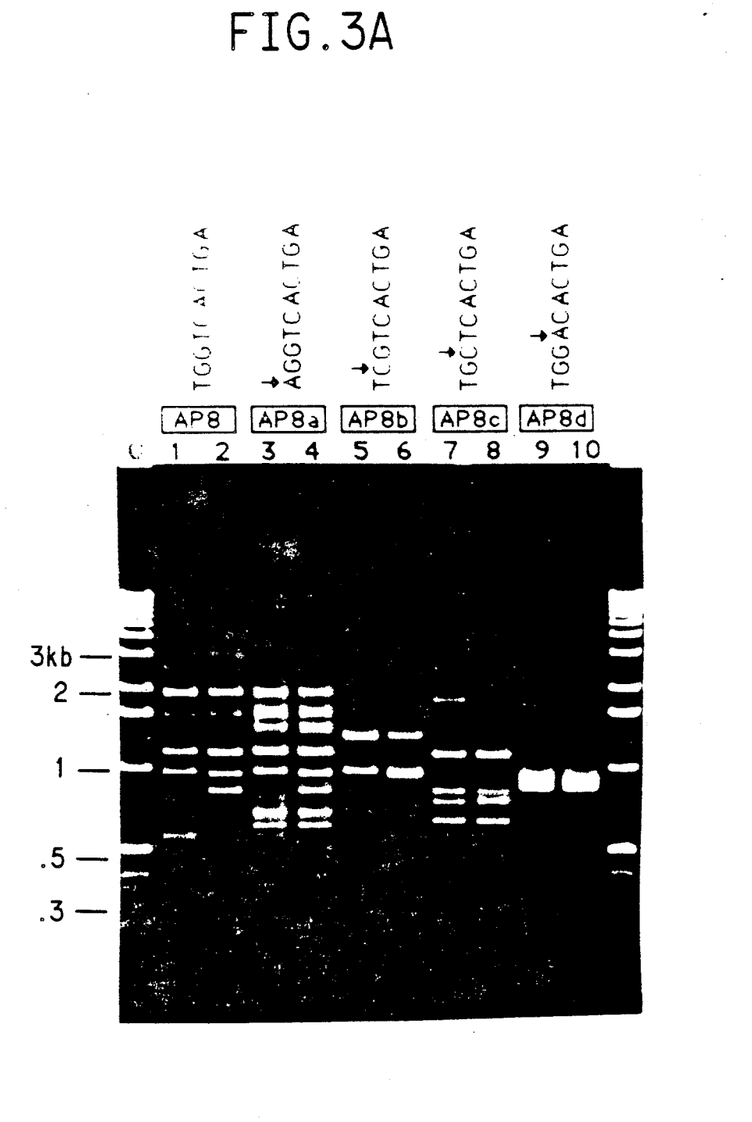
Figure 3B:
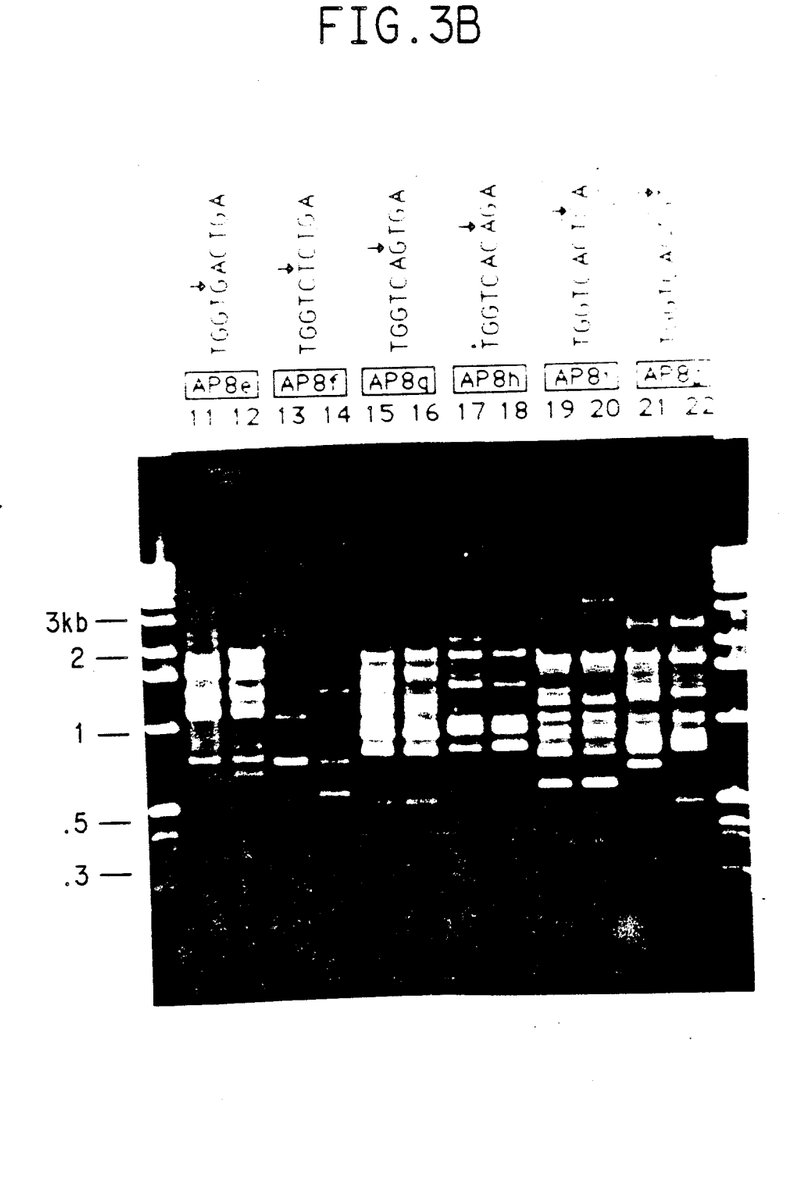

FIG. 3 is a photograph of the stained electrophoresis gel. Lane 0 is a molecular weight standard. DNA amplification products are shown for Bonus (odd numbered lanes) and for PI 81762 (even numbered lanes). Arrows mark the location in each primer that differs from the sequence of primer AP8. Each primer generated very different patterns of amplified DNA segments with the exception of AP8 and AP8-a which appeared to differ qualitatively in only 1 band (see 250 bp bands found only with AP8-a; FIG. 3, lanes 1-4). Whereas the overall pattern of bands differed for the majority of primers, there were at least some bands that may be common to different primers (note polymorphic 1 kb bands that appear to be amplified by AP8, AP8-a and AP8-b; FIG. 3, lanes 1-6). Except for primers AP8 and AP8-a, different polymorphisms between Bonus and PI 81762 were revealed with each primer. Among the patterns generated by all 11 primers, there were about 22 distinct polymorphisms as defined by the presence of a band in one genome and its corresponding absence in the other genome.

A few exceptions notwithstanding, a single nucleotide change in a primer generally produced a significant change in the pattern of amplified bands and revealed new polymorphisms. This suggests that the conditions of this experiment are sufficiently stringent so as to require the participation of most, if not all, of the bases in a given primer.

EXAMPLE 5

Amplification of DNA from various species with 10 nucleotide primers of arbitrary sequence In this Example, genomic DNA was tested from cotton (line #315, Coker Seed Co., Hartsville, S.C. 29550), yeast (line DBY931, E. I du Pont de Nemours & Co., Wilmington, Del.), *Arabidopsis* (line W5, see K. A. Feldman et al., *Science*, (1989) 243:1351–1354) and corn (line B73 University of Illinois). DNA samples were prepared by standard methods as follows: *Gossypium hirsutum* (cotton), R. Bernatzky and S. D. Tanksley 1986, *Theor. Appl. Genet.* 72, 314–321; *Sacchoromyces cerevisiae* (yeast), R. W. Davis, M.-Thomas, J. Cameron, T. P. St. John, S. Scherer and R.-A. Padget 1980, *Methods Enzymol.* 65, 404–411; *Arabidopsis thaliana* (Arabidopsis), Shure, Wessler, Fedoroff, 1983, *Cell*, 35, 225-233; and *Zea mays* (corn), Dellaporta, S. L. "Molecular Biology of Plants a Laboratory Course Manual," *Cold Spring Harbor, N.Y.*, 11724 (1985), pp. 36-37. Reaction ingredients were used at the concentrations specified in Example 2, and were prepared as shown in Table V.

TABLE V

| Cocktail | Volume μl |
| --- | --- |
| Deionized water | 1837.0 |
| 10x Buffer | 550.0 |
| MgCl₂, 1M | 5.5 |
| Mixture of dATP, dCTP, dGTP, TTP, 1.25 mM each | 880.0 |
| Amplitaq polymerase, 5 units/μl | 27.0 |

Primers AP3, AP4, AP5, AP6, AP7 and AP8 (Table I) were diluted with water to concentrations of 2 μM. Genomic DNA samples were diluted with water to concentrations of 10 mg/ml, were heated at 99° C. for 4 minutes in the Perkin-Elmer cycler, and cooled to room temperature prior to use. Reaction mixtures for amplification were prepared in a PVC 96-well plate by mixing 10 μl of genomic DNA, 10 μl of primer Table I, and 30 μl of cocktail Table V. All sample wells were utilized and all were overlayed with a drop (40 μl) of mineral oil. Thermal cycling was in the cycling oven, as described in Example 4. Annealing temperature was programmed at 36° C.

Figure 4:
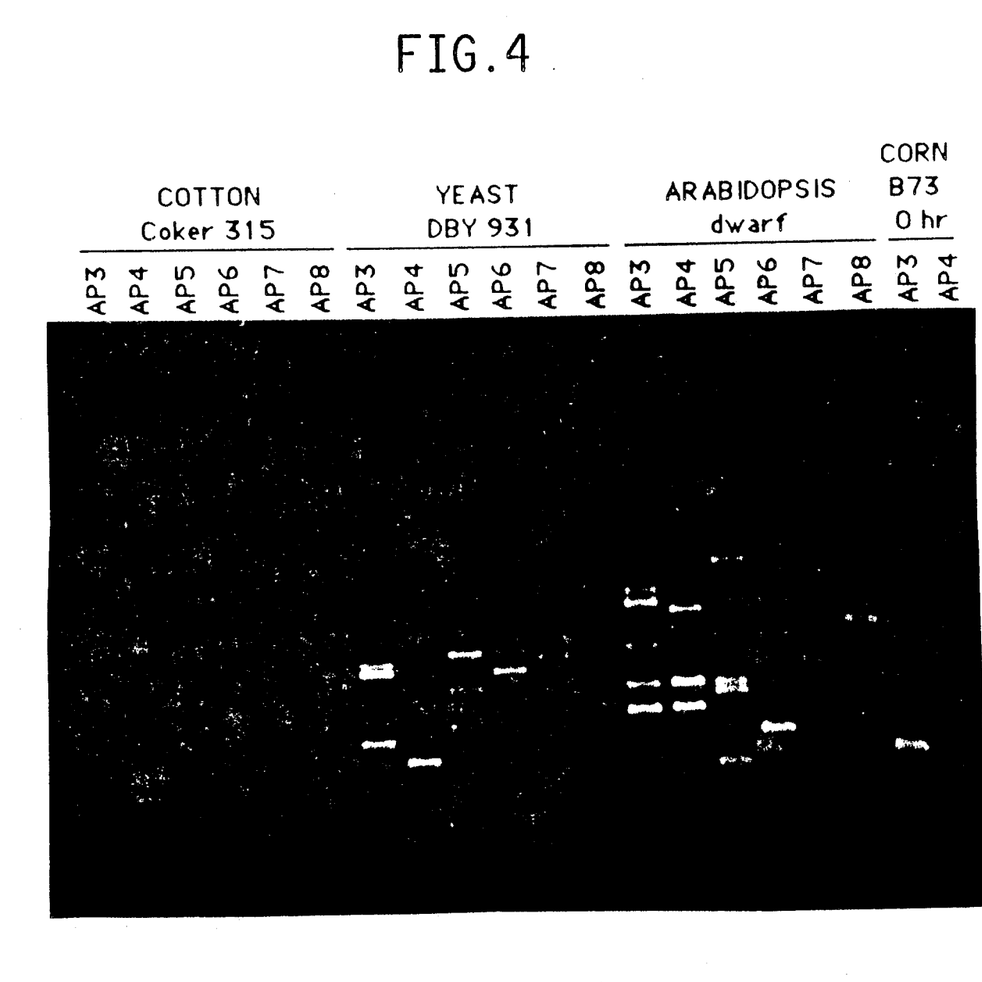
FIG. 4 illustrates a photograph of a gel comparing amplification products employing a variety of primers on *Zea mays* (corn), *Gossypium hirsutum* (cotton), *Sacchoromyces cerevisiae* (yeast) and *Arabidopsis. thaliana* DNA.

Amplification reaction products were analyzed by agarose gel electrophoresis as in Example 3. FIG. 4 illustrates a photograph of a stained electrophoresis gel. Lanes 1-6 are DNA amplification products from cotton, Lanes 7-12 from yeast, Lanes 13-18 from Arabidopsis and Lanes 19-20 from corn. The results show that all of the genomic DNA samples were successfully amplified by most of the tested primers. This is surprising in view of the small genome sizes of yeast and arabidopsis relative to that of cotton, corn and soybean.

EXAMPLE 6

Primers greater than 7 nucleotides support DNA amplification

In this Example, six different primers between 6 and 10 nucleotides in length (Table VII) were compared for the ability to function as primers in the amplification reaction. Reaction ingredients were as described in Example 2 and were prepared as shown in Table VI.

TABLE VI

| Genomic DNA Cocktail | Volume μl | |
| --- | --- | --- |
| | Bonus | PI81762 |
| Deionized water | 1240 | 1242 |
| 10x Buffer | 175 | 175 |
| MgCl₂, 200 mM | 3.5 | 3.5 |
| Mixture of dATP, dCTP, dGTP, TTP, 1.25 mM each | 140 | 140 |
| Amplitaq polymerase, 5 units/μl | 9 | 9 |
| Bonus DNA, 448 μg/ml | 7.8 | — |
| PI 81762 DNA, 670 μg/ml | — | 7.8 |

TABLE VII

| Primer Sequence | Primer Name | Conc. of Stock Solution |
| --- | --- | --- |
| 5'-ATTGCGTCCA | AP13 | 4 μM |
| 5'-TTGCGTCCA | AP13a | 4 μM |
| 5'-TGCGTCCA | AP13b | 4 μM |
| 5'-GCGTCCA | AP13c | 4 μM |

TABLE VII-continued

| Primer Sequence | Primer Name | Conc. of Stock Solution |
| --- | --- | --- |
| 5'-CGTCCA | AP13d | 4 μM |
| 5'-CGCCCA | AP13e | 4 μM |

Primer AP13 was an arbitrary sequence of 50% A plus T as in Example 1. Primers AP13a through AP13e were designed by sequentially removing nucleotides from the 5' end. Primer AP13c had an additional T substituted by a C to lend stability.

Each primer (2.5 μl) was mixed separately in 0.6 ml microcentrifuge tubes as in Example 2 with 22.5 μl of each cocktail containing template DNA from either Bonus or PI 81762. Each mixture was overlayed with 40 μl of mineral oil (Example 2). Temperature cycling was performed in a DNA Thermal Cycler (Perkin Elmer-Cetus, Norwalk, Conn.) for 35 cycles with parameters set at: hold 94° C. for 1 min, hold 35° C. for 1 min, ramp to 72° C. in 2 min, hold 72° C. for 2 min. After the amplification reaction of the present invention was complete, 12 μl of each sample was analyzed by electrophoresis on a 1.4% agarose gel as described in Example 2.

Figure 5:
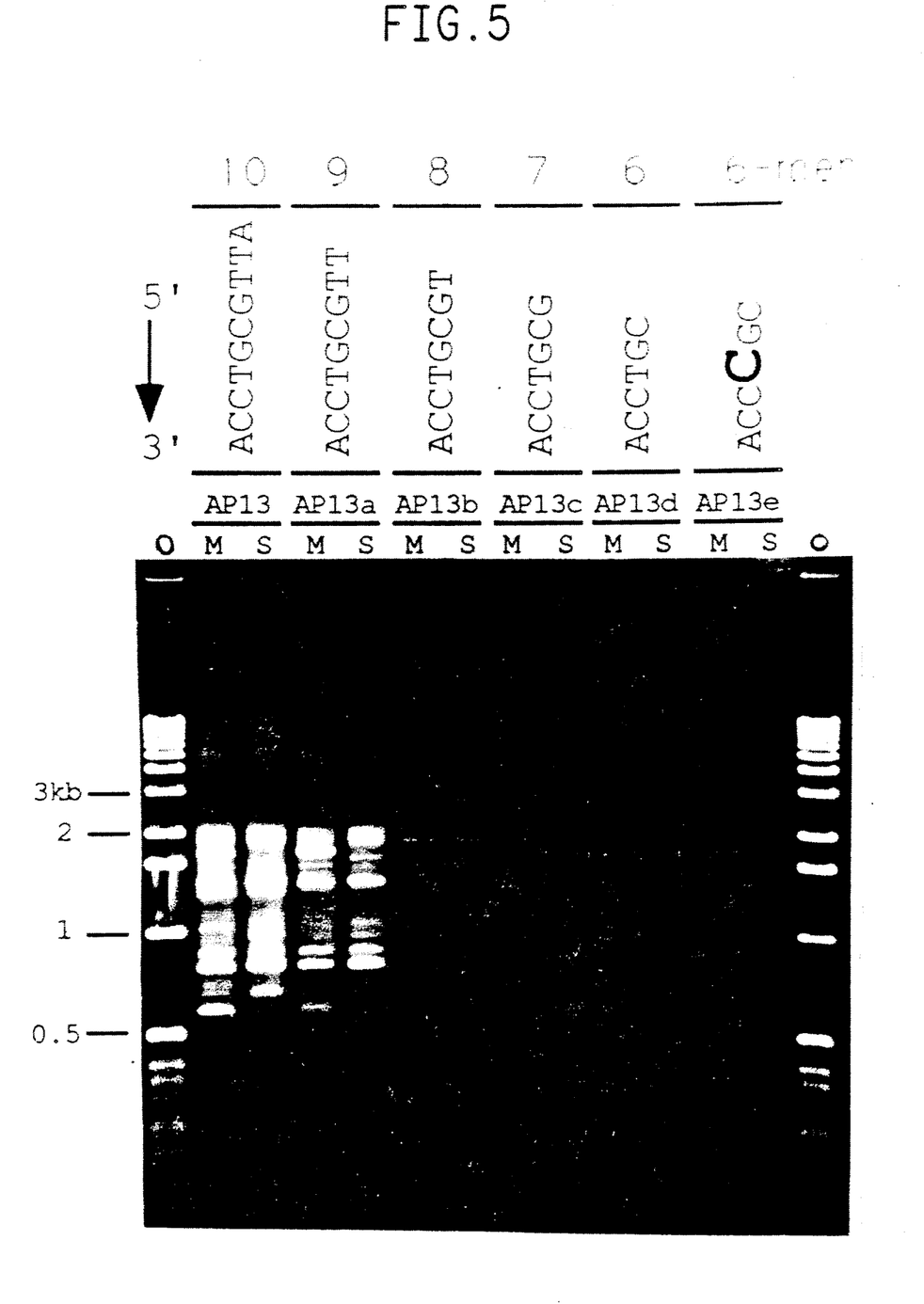
FIG. 5 illustrates a photograph of a gel demonstrating amplification by priming with primers of six to ten nucleotides in length.

FIG. 5 is a photograph of a stained electrophoresis gel. Lane 0 is a molecular weight standard. The results indicate that under the chosen conditions of amplification, primers shorter than 8 nucleotides do not support detectable levels of amplification.

EXAMPLE 7

Amplification of human DNA with a nucleotide primer of arbitrary sequence (AP9)

TABLE VIII

| Cocktail | Volume μl |
| --- | --- |
| Deionized water | 103.5 |
| 10x Buffer* | 45.0 |
| MgCl₂, 50 mM | 9.0 |
| Mixture of dATP, dCTP, dGTP, TTP, 2 mM each | 45.0 |
| AP9 primer, 10 μM (see Example 2) | 18.0 |
| AmpliTaq polymerase, 5 units/μl | 4.5 |

*(The 10x Buffer used here consists of 100 mM Tris-HCl, ph 8.3; 500 mM KCl; 15 mM MgCl₂; 50 μM EDTA; 0.1% gelatin.)

Twenty-five microliters of cocktail (Table VIII) were dispensed to each of seven reaction tubes. The genomic DNA samples prepared from transformed lymphoblasts were from six anonymous individuals and are designated Hul-6. The genomic DNA samples were obtained from Drs. John Gilbert and Allen Roses of Duke Medical Center, Durham, N.C. Each genomic DNA sample was prepared by adding 100 ng DNA (2-3 μl) to 25 μl H₂O, heating in a boiling water bath for 1 min, and placing on ice. For each amplification reaction, 25 μl DNA was added to the reaction cocktail. Also, a blank reaction was prepared by adding 25 μl H₂O to a tube containing reaction cocktail. The reactions were overlayed with a drop of mineral oil. Temperature cycling was performed in a DNA Thermal Cycler according to the following program: an initial 4 min incubation at 93° C.; cycles of 1 min at 93° C.; 30 sec at 35° C.; 2 min 10 sec ramp to 72° C.; 2 min at 72° C.; followed by a final 5 min incubation at 72° C. After transferring to fresh tubes, 50 μl 5M ammonium acetate and 250 μl ethanol were added to each sample. Following a 2 hour incubation at −20° C., each DNA sample was collected by centrifugation, dried, and dissolved in 20 μl mM Tris-HCl, pH 8.0; 1 mM EDTA.

Figure 6:
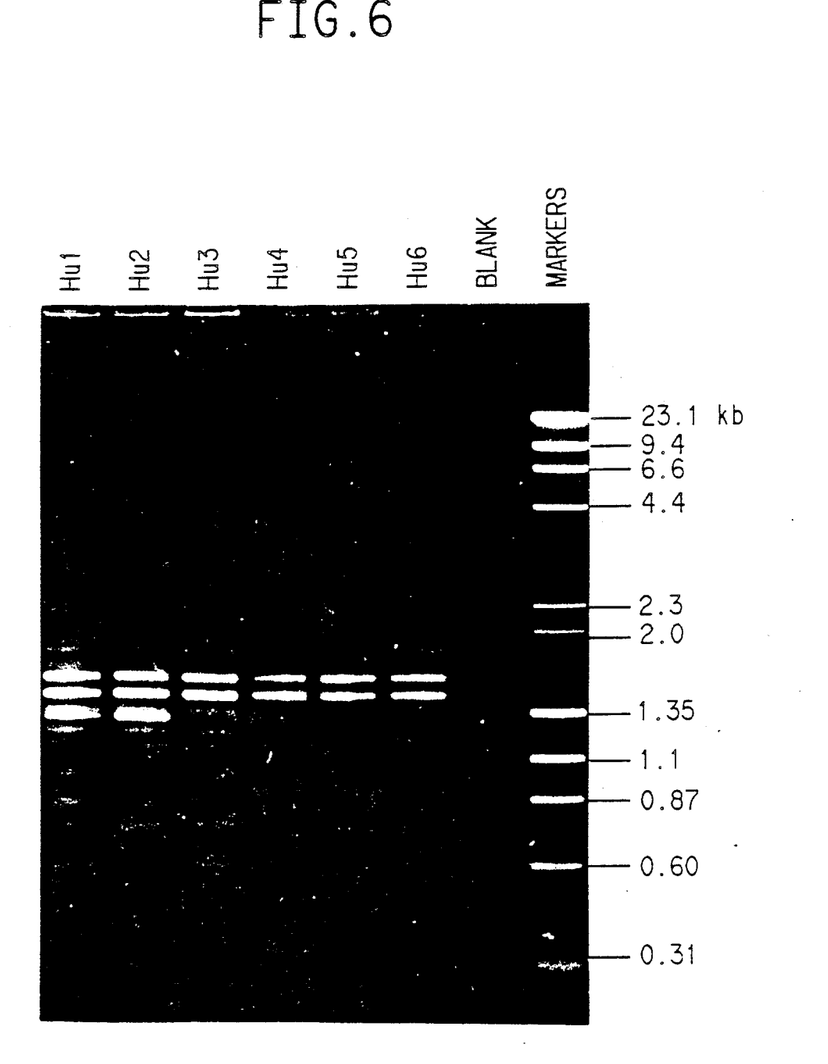
FIG. 6 illustrates a photograph of a gel comparing amplification products from six transformed *Homo sapien* (human) lymphoblasts.

Two microliters of each sample were electrophoresed on a 1.4% agarose gel (8.3-cm × 6 cm) in TAE buffer (40 mM Tris-acetate, pH 7.8; 5 mM sodium acetate: 1 mM ESTA) at 50 V for 160 min. After staining with ethidium, the gel was photographed using ultraviolet illumination. The results in FIG. 6 show that samples Hu1 and Hu2 have a prominent band at approximately 1.3 kb that is not present in the four other samples. Thus, amplification using the 10 nucleotide primer AP9 was able to detect a genetic polymorphism that can be used to distinguish human DNA samples.

EXAMPLE 8

Quantitation of PCR Products

Figure 7A:
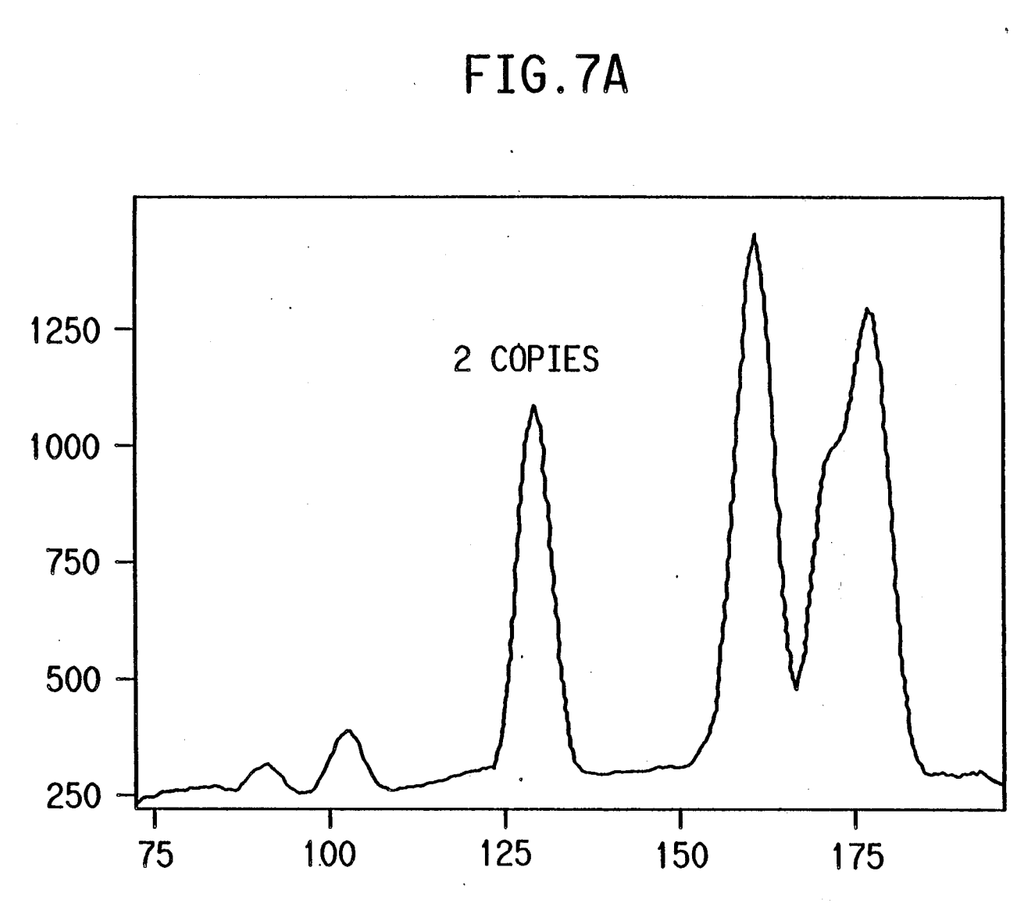
FIG. 7A-7C illustrate densitometric scans demonstrating F2 individuals of a cross between Bonus and PI 81762 homozygous (2 copies) for a polymorphism (FIG. 7A), heterozygous for a polymorphism (FIG. 7B) and homozygous (0 copies) for a polymorphism (FIG. 7C).
Figure 7B:
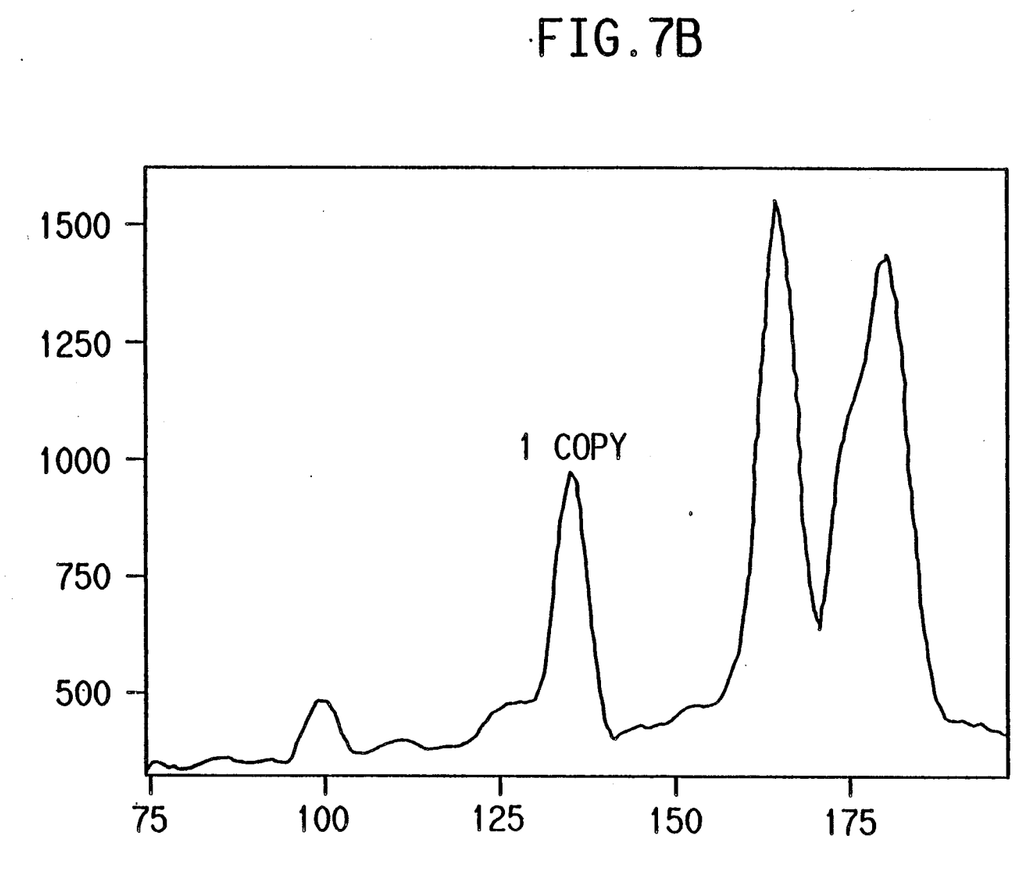
Figure 7C:
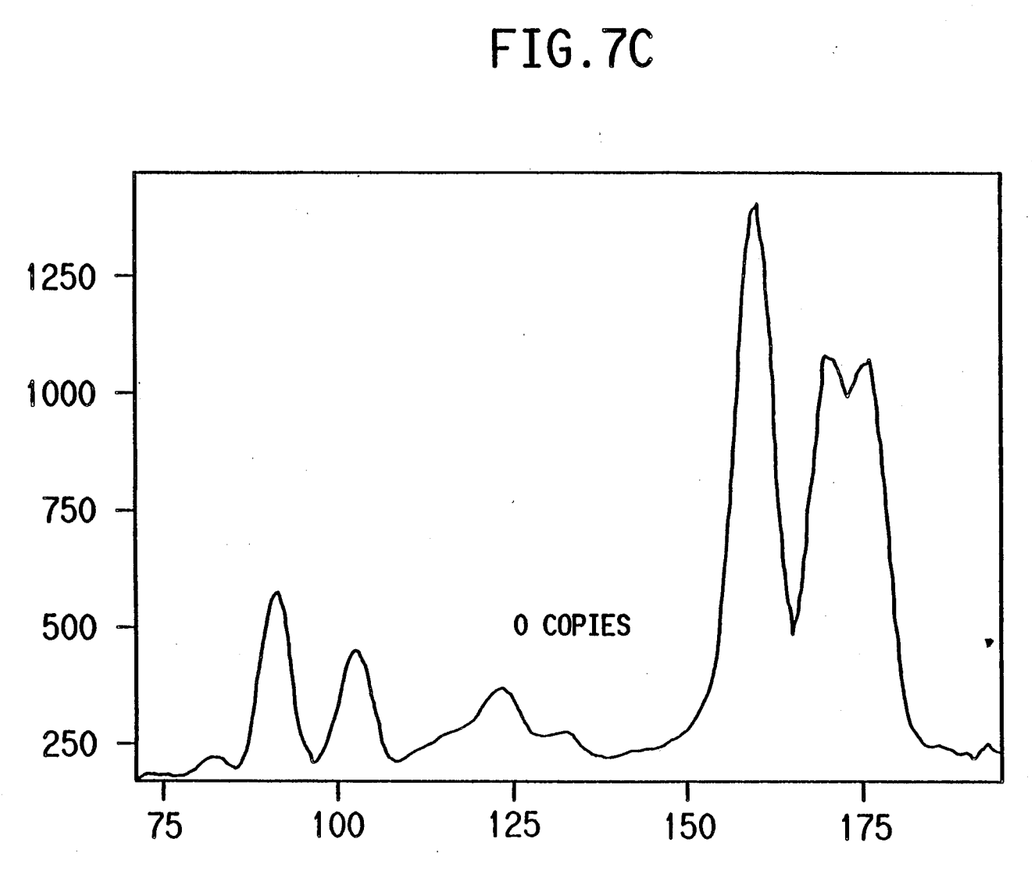

In Example 3, the process of this invention was used to genetically map a polymorphism. This was accomplished by determining the parental pattern of inheritance of the polymorphism in several segregating individuals. As practiced in Example 3, the investigator is unable to distinguish individuals heterozygous for a marker from individuals homozygous for the same marker, and the polymorphism is scored as being dominant. A heterozygous individual contains two different copies (alleles) of a particular DNA segment at a position (locus) in the genome. A homozygous individual will contain two identical alleles at a locus. In several applications (e.g., quantitative trait mapping) it is necessary to be able to distinguish heterozygous individuals. In the process of the present invention, it is expected that individuals inheriting two copies of a single allele will have two times the amount of amplified product as an individual inheriting only one copy of the same allele. To investigate whether heterozygotes could be distinguished from homozygotes by quantitating the results of the assay, individuals were chosen which were known to be homozygous for Bonus, heterozygous for both Bonus and PI81762 or homozygous for PI81762 DNA segments for the chromosomal region containing the band A polymorphism. These individuals were chosen on the basis of the genotype of flanking RFLP markers (see Example 3 and Table 3). The same gels presented in Example 3 were analyzed by densitometry to determine the amount of amplified product corresponding to band A (see legend to FIG. 7). Panel A of FIG. 7 represents a scan of individual 30 (see Example 3) homozygous for the PI81762 allele. Panel B of FIG. 7 represents a scan of individual 9 (see Example 3) heterozygous for Bonus and PI81762 alleles. Panel C of FIG. 7 represents a scan of individual 57 (see Example 3) homozygous for the Bonus allele. Peaks corresponding to the band A polymorphism are labeled. The densitometry shows that individuals homozygous for PI81762 alleles contain twice the amount of DNA in the band A polymorphism than individuals which are heterozygous for PI81762 and Bonus. Individuals homozygous for the Bonus alleles do not contain any DNA corresponding to band A. This example shows that the products of amplification can be quantitated to identify heterozygous individuals and reveal a co-dominant polymorphism. This will have utility in procedures where it is necessary to distinguish heterozygotes from the corresponding homozygote.

Photographs of the gel separations shown in FIG. 2 were digitized using a Cohu Monochrome CCD camera (model #4815-5000, Cohu Inc., San Diego, Calif.) attached to a Macintosh IIcx computer (Apple Computer Corp., Cupertino, Calif.). The analog data was converted to digital input through a QuickCapture card (Data Translations Inc., Marlboro, Mass.). The individual lanes were scanned for quantitation with the Scan Analysis program (Version 2.11, Biosoft Inc., Milltown, N.J.). X-axis values correspond to electrophoretic distance, and Y-axis values correspond to peak intensity.

What is claimed is:

1. A process for detecting polymorphisms on the basis of nucleotide differences in random segments of nucleic acids comprising:
   (a) separately performing an extension reaction on a random segment of each of at least two nucleic acids from different sources, said reaction comprising:
      (i) contacting each of the nucleic acids with at least one nonspecifically targeted oligonucleotide primer of greater than 7 nucleotides under conditions such that for at least one nucleic acid a random extension product of at least one primer is synthesized; and
   (b) comparing the results of the separately performed random extension reactions for differences.

2. The process of claim 1, after step (i) and before step (b), further comprising the additional steps of (ii) dissociating the extension product from its complement; and (iii) amplifying the random nucleic acid segment by contacting the dissociated extension product with at least one primer of step (i) under conditions such that an amplification extension product is synthesized using the dissociated extension product as a template.

3. The process of claim 2 wherein the steps are performed at least twice.

4. The process of claim 1 or 2 using a nucleic acid polymers and nucleoside triphosphate substrates or their analogues and mixtures thereof.

5. The process of claim 1 or 2 wherein one primer is employed.

6. The process of claim 1 or 2 wherein the primer is from 9 to 10 nucleotides in length.

7. The process of claim 1 or 2 wherein at least one primer is biotinylated.

8. The process of claim 1 or 2 wherein the nucleic acids are from different individual organisms.

9. A process according to claim 4, wherein the nucleic acid polymerase is a DNA polymerase and the nucleoside triphosphate substrates are deoxyribonucleoside triphosphate substrates.

10. A process according to claim 9, wherein the DNA polymerase is a thermostable polymerase.

11. A process according to claim 10, wherein the DNA polymerase is Taq polymerase.

12. The process of claim 1 or 2, wherein the comparison is through size separation of the random extension products.

13. A process according to claim 12, wherein the size separation comparison is performed by electrophoresis through a polyacrylamide gel matrix or agarose gel matrix.

14. The process of claim 1 or 2, wherein the comparison is through nucleotide sequence determination.

15. The process of claim 1 or 2, wherein the nucleic acid source is selected from the group consisting of plants, animals and microbes.

16. The process of claim 1 or 2 wherein the nucleic acid source is human.

17. The process of claim 1 or 2 wherein a difference in the random extension products is used as a marker to construct a genetic map.

18. The process of claim 1 or 2 wherein a difference in the random extension products is used as a marker to distinguish or identify individuals.

* * * * *